(12) United States Patent
Dubreuil et al.

(10) Patent No.: US 10,501,694 B2
(45) Date of Patent: Dec. 10, 2019

(54) SELECTIVE HYDROGENATION PROCESS USING A NICKEL CATALYST PREPARED WITH AN ADDITIVE CONTAINING AN AMINE OR AMIDE FUNCTION OR AN AMINO ACID

(71) Applicant: IFP Energies nouvelles, Rueil-Malmaison (FR)

(72) Inventors: Anne-Claire Dubreuil, Lyons (FR); Agathe Martel, Lyons (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/852,337

(22) Filed: Dec. 22, 2017

(65) Prior Publication Data
US 2018/0179452 A1  Jun. 28, 2018

(30) Foreign Application Priority Data
Dec. 22, 2016 (FR) ..................... 16 63092

(51) Int. Cl.
| C10G 45/36 | (2006.01) |
| B01J 37/02 | (2006.01) |
| C07C 7/163 | (2006.01) |
| B01J 23/755 | (2006.01) |
| B01J 37/08 | (2006.01) |
| B01J 35/00 | (2006.01) |
| B01J 35/10 | (2006.01) |
| B01J 31/02 | (2006.01) |
| B01J 31/04 | (2006.01) |
| B01J 21/04 | (2006.01) |

(52) U.S. Cl.
CPC ............ *C10G 45/36* (2013.01); *B01J 23/755* (2013.01); *B01J 31/0238* (2013.01); *B01J 31/0247* (2013.01); *B01J 31/04* (2013.01); *B01J 35/002* (2013.01); *B01J 35/006* (2013.01); *B01J 35/1014* (2013.01); *B01J 35/1042* (2013.01); *B01J 37/0203* (2013.01); *B01J 37/0205* (2013.01); *B01J 37/0236* (2013.01); *B01J 37/08* (2013.01); *B01J 37/084* (2013.01); *B01J 37/088* (2013.01); *C07C 7/163* (2013.01); *B01J 21/04* (2013.01); *B01J 2231/645* (2013.01); *B01J 2523/00* (2013.01); *B01J 2531/847* (2013.01)

(58) Field of Classification Search
CPC ... C10G 45/36; B01J 37/0203; B01J 37/0205; B01J 37/0236; B01J 37/024; B01J 37/08
USPC ......................................... 585/259
See application file for complete search history.

(56) References Cited

U.S. PATENT DOCUMENTS

| 3,215,750 | A | * | 11/1965 | Benesi | ............. B01J 23/00 585/271 |
| 4,229,361 | A | * | 10/1980 | Cahen | ............. B01J 23/755 554/145 |
| 9,328,039 | B2 | | 5/2016 | Diehl | |
| 9,783,745 | B2 | * | 10/2017 | Corvaisier | ........ B01J 23/75 |
| 2009/0318739 | A1 | * | 12/2009 | Liu | ............. B01J 23/883 585/276 |
| 2013/0150639 | A1 | * | 6/2013 | Diehl | ............. B01J 23/755 585/265 |

FOREIGN PATENT DOCUMENTS

| FR | 2963344 A1 | 2/2012 |
| FR | 2994661 A1 | 2/2014 |
| FR | 3035008 A1 | 10/2016 |

\* cited by examiner

*Primary Examiner* — Philip Y Louie
(74) *Attorney, Agent, or Firm* — Millen, White, Zelano and Branigan, P.C.

(57) ABSTRACT

Selective hydrogenation of polyunsaturated compounds containing at least 2 carbon atoms per molecule contained in a hydrocarbon feed with a final boiling point of 300° C. or less, in the presence of a catalyst having a support formed from alumina and an active phase constituted by nickel, said catalyst being prepared by:
i) bringing said support into contact with at least one solution containing at least one precursor of nickel;
ii) bringing said support into contact with at least one solution containing at least one organic compound comprising at least one amine function with the empirical formula $C_xN_yH_z$ in which x is in the range 1 to 20, $y=1-x$ and $z=2-2x+2$, or an amide function, or an amino acid,
iii) drying said impregnated support at a temperature of less than 250° C.;
steps i) and ii) being carried out separately, in any order, or simultaneously.

16 Claims, No Drawings

SELECTIVE HYDROGENATION PROCESS USING A NICKEL CATALYST PREPARED WITH AN ADDITIVE CONTAINING AN AMINE OR AMIDE FUNCTION OR AN AMINO ACID

FIELD OF THE INVENTION

The invention relates to a process for the selective hydrogenation of polyunsaturated compounds in a hydrocarbon feed, in particular in C2-C5 cuts from steam cracking and gasolines from steam cracking, in the presence of a nickel catalyst supported on an alumina support prepared by means of an organic additive comprising at least one amine or amide type function.

PRIOR ART

Catalysts for the selective hydrogenation of polyunsaturated compounds are generally based on metals from group VIII of the periodic classification of the elements such as nickel. The metal is in the form of nanometric metallic particles deposited on a support which may be a refractory oxide. The group VIII metal content, the optional presence of a second metallic element, the size of the metal particles and the distribution of the active phase in the support as well as the nature and pore distribution of the support are parameters which may be of importance as regards the performances of the catalysts.

The rate of the hydrogenation reaction is governed by a number of criteria, such as the diffusion of the reagents towards the surface of the catalyst (external diffusional limitations), the diffusion of the reagents in the pores of the support towards the active sites (internal diffusional limitations) and the intrinsic properties of the active phase, such as the size of the metallic particles and the distribution of the active phase in the support.

Regarding the size of the metallic particles, it is generally assumed that the catalyst becomes more active as the size of the metallic particles becomes smaller. In addition, it is important to obtain a particle size distribution which is centred on the optimal value as well as a narrow distribution about this value.

With the aim of obtaining better catalytic performances, in particular better selectivity and/or activity, it is known in the prior art to use additives of the organic compound type in order to prepare metallic selective hydrogenation catalysts. As an example, the application FR 2 984 761 discloses a process for the preparation of a selective hydrogenation catalyst comprising a support and an active phase comprising a metal from group VIII, said catalyst being prepared by a process comprising a step for impregnationion of a solution containing a precursor of a metal from group VIII and an organic additive, more particularly an organic compound containing one to three carboxylic acid functions, a step for drying the impregnated support, and a step for calcining the dried support in order to obtain the catalyst.

The patent FR 2 963 344 discloses the use of organic compounds comprising a cyclic oligosaccharide composed of at least 6 α-(1,4)-bonded glucopyranose sub-units.

In this context, one of the aims of the present invention is to propose a process for the selective hydrogenation of polyunsaturated compounds such as diolefins and/or acetylenes and/or alkenylaromatics in the presence of a supported catalyst with a nickel active phase, prepared by means of a particular organic additive which can be used to obtain hydrogenation performances in terms of activity which are at least as good or even better than prior art processes which are known in the art.

The Applicant has discovered that a catalyst comprising an active phase constituted by nickel supported on alumina prepared using a specific organic additive of the amine or amide or amino acid type, when it is used in a selective hydrogenation process, exhibits improved catalytic performances in terms of catalytic activity. This leads to better conversion of the feed under identical operating conditions.

AIMS OF THE INVENTION

The present invention concerns a process for the selective hydrogenation of polyunsaturated compounds containing at least 2 carbon atoms per molecule, such as diolefins and/or acetylenes and/or alkenylaromatics, contained in a hydrocarbon feed selected from the C2 cut from steam cracking, the C2-C3 cut from steam cracking, the C3 cut from steam cracking, the C4 cut from steam cracking, the C5 cut from steam cracking and gasolines from steam cracking, with a final boiling point of 300° C. or less, said process being carried out at a temperature in the range 0° C. to 300° C., at a pressure in the range 0.1 to 10 MPa, at a molar ratio of hydrogen/(polyunsaturated compounds to be hydrogenated) in the range 0.1 to 10 and at an hourly space velocity in the range 0.1 to 200 $h^{-1}$ when the process is carried out in the liquid phase, at a molar ratio of hydrogen/(polyunsaturated compounds to be hydrogenated) in the range 0.5 to 1000 and at an hourly space velocity in the range 100 to 40000 $h^{-1}$ when the process is carried out in the gas phase, in the presence of a catalyst comprising a support formed from alumina and an active phase constituted by nickel, said catalyst being prepared by means of a process comprising at least:

i) a step for bringing said support into contact with at least one solution containing at least one precursor of nickel;
ii) a step for bringing said support into contact with at least one solution containing at least one organic compound comprising at least one amine function with the empirical formula $C_xN_yH_z$ in which $1 \leq x \leq 20$, $1 \leq y \leq x$, $2 \leq z \leq 2x+2$, or at least one amide function, or at least one amino acid,
iii) a step for drying said impregnated support at a temperature of less than 250° C.; steps i) and ii) being carried out separately, in any order, or simultaneously.

In accordance with one embodiment of the invention, the process may furthermore comprise at least one step iv) for calcining said dried catalyst obtained in step iii) at a temperature in the range 250° C. to 1000° C.

In one embodiment of the invention, steps i) and ii) of the process in accordance with the invention are carried out simultaneously.

In another embodiment of the invention, step i) of the process in accordance with the invention is carried out before step ii).

In yet another embodiment of the invention, step ii) of the process in accordance with the invention is carried out before step i).

Preferably, steps i) and/or ii) is (are) carried out by dry impregnation.

Advantageously, the nickel content is in the range 1% to 35% by weight with respect to the total catalyst weight.

Advantageously, said organic compound contains in the range 1 to 20 carbon atoms.

In accordance with one embodiment of the invention, said organic compound comprises at least one amine function with the empirical formula $C_xN_yH_z$ in which $1 \leq x \leq 20$, $1 \leq y \leq x$, $2 \leq z \leq 2x+2$.

Preferably, said organic compound contains in the range 1 to 3 amine functions.

In accordance with one embodiment of the invention, said organic compound comprises at least one amine function and at least one carboxylic acid function.

In accordance with one embodiment of the invention, said organic compound comprises at least one amide function selected from an acyclic amide function or a cyclic amide function or a lactam type amide function.

In one embodiment in accordance with the invention, said organic compound comprises at least one amide function and at least one other function which differs from the amide function selected from a carboxylic acid function or an alcohol function.

In another embodiment in accordance with the invention, said organic compound furthermore comprises a supplemental nitrogen heteroatom and is selected from urea, N-methylurea, N,N'-dimethylurea, 1,1-dimethylurea and tetramethylurea, in any one of their isomeric forms.

In one embodiment in accordance with the invention, the process in accordance with the invention is carried out in the presence of a feed selected from a C2 cut from steam cracking or a C2-C3 cut from steam cracking, and in which process the molar ratio of (hydrogen)/(polyunsaturated compounds to be hydrogenated) is in the range 0.5 to 1000, the temperature is in the range 0° C. to 300° C., the hourly space velocity (HSV) is in the range 100 to 40000 h$^{-1}$, and the pressure is in the range 0.1 to 6.0 MPa.

In one embodiment in accordance with the invention, the process in accordance with the invention is carried out in the presence of a feed selected from the gasolines from steam cracking and in which process the molar ratio of (hydrogen)/(polyunsaturated compounds to be hydrogenated) is in the range 0.5 to 10, the temperature is in the range 0° C. to 200° C., the hourly space velocity (HSV) is in the range 0.5 to 100 h$^{-1}$, and the pressure is in the range 0.3 to 8.0 MPa.

DETAILED DESCRIPTION

Definitions

In the remainder of the text, the groups for the chemical elements are given in accordance with the CAS classification (CRC Handbook of Chemistry and Physics, published by CRC press, Editor-in-Chief D. R. Lide, 81$^{st}$ edition, 2000-2001). As an example, group VIII in accordance with the CAS classification corresponds to metals from columns 8, 9 and 10 in accordance with the new IUPAC classification.

The textural and structural properties of the support and of the catalyst described below are determined by characterization methods which are known to the person skilled in the art. The total pore volume and the pore distribution are determined in the present invention by nitrogen porosimetry as described in the publication "Adsorption by Powders & Porous Solids: Principles, Methodology and Applications", written by F Rouquerol, J Rouquerol and K Singh, Academic Press, 1999.

The term "specific surface area" means the BET specific surface area ($S_{BET}$ in m$^2$/g) determined by nitrogen adsorption in accordance with the ASTM standard D 3663-78 based on the BRUNAUER-EMMETT-TELLER method described in the periodical "*The Journal of the American Society*" 1938, 60, 309.

The term "size of the nanoparticles of nickel" means the diameter of the crystallites of nickel in the oxide form. The mean diameter of the crystallites of nickel in the oxide form is determined by X ray diffraction starting from the width of the diffraction peak located at the angle 2theta=43° (i.e. in the [200] crystal plane) using the Scherrer relationship. This method, which is used in X ray diffraction on powders or polycrystalline samples, which links the width at mid-height of the diffraction peaks to the particle size, is described in detail in the reference: Appl. Cryst. (1978), 11, 102-113 "Scherrer after sixty years: A survey and some new results in the determination of crystallite size", J. I. Langford and A. J. C. Wilson.

Description of the Process

The present invention concerns a process for the selective hydrogenation of polyunsaturated compounds containing at least 2 carbon atoms per molecule, such as diolefins and/or acetylenes and/or alkenylaromatics, also known as styrenes, contained in a hydrocarbon feed selected from the C2 cut from steam cracking, the C2-C3 cut from steam cracking, the C3 cut from steam cracking, the C4 cut from steam cracking, the C5 cut from steam cracking and gasolines from steam cracking, with a final boiling point of 300° C. or less, said process being carried out at a temperature in the range 0° C. to 300° C., at a pressure in the range 0.1 to 10 MPa, at a molar ratio of hydrogen/(polyunsaturated compounds to be hydrogenated) in the range 0.1 to 10 and at an hourly space velocity in the range 0.1 to 200 h$^{-1}$ when the process is carried out in the liquid phase, or with a molar ratio of hydrogen/(polyunsaturated compounds to be hydrogenated) in the range 0.5 to 1000 and at an hourly space velocity in the range 100 to 40000 h$^{-1}$ when the process is carried out in the gas phase, in the presence of a catalyst comprising a support formed from alumina and an active phase constituted by nickel, said catalyst being prepared by means of a process comprising at least:

i) a step for bringing said support into contact with at least one solution containing at least one precursor of nickel;

ii) a step for bringing said support into contact with at least one solution containing at least one organic compound comprising at least one amine function with the empirical formula $C_xN_yH_z$ in which $1 \leq x \leq 20$, $1 \leq y \leq x$, $2 \leq z \leq 2x+2$, or an amide function, or an amino acid, iii) a step for drying said impregnated support at a temperature of less than 250° C., in order to obtain a dried catalyst;

steps i) and ii) being carried out separately, in any order, or simultaneously.

Monounsaturated organic compounds such as ethylene and propylene, for example, are sources for the manufacture of polymers, plastic materials and other chemical products of added value. These compounds are obtained from natural gas, naphtha or gas oil which have been processed by means of steam cracking or catalytic cracking processes. These processes are operated at high temperature and, in addition to the desired monounsaturated compounds, produce polyunsaturated organic compounds such as acetylene, propadiene and methylacetylene (or propyne), 1-2-butadiene and 1-3-butadiene, vinylacetylene and ethylacetylene, and other polyunsaturated compounds with a boiling point corresponding to the C5+ cut (hydrocarbon compounds containing at least 5 carbon atoms), in particular diolefinic compounds or styrene compounds or indene compounds. These polyunsaturated compounds are highly reactive and lead to side reactions in the polymerization units. Thus, it is necessary to eliminate them before upgrading these cuts.

Selective hydrogenation is the principal treatment which has been developed in order to specifically eliminate unwanted polyunsaturated compounds from these hydrocarbon feeds. It can be used to convert polyunsaturated compounds into the corresponding alkenes or aromatics, avoiding their complete saturation and thus the formation of the corresponding alkanes or naphthenes. In the case of steam cracked gasolines used as the feed, selective hydrogenation can also be used to selectively hydrogenate the alkenylaromatics into aromatics, avoiding hydrogenation of the aromatic rings.

The feed of hydrocarbons processed in the selective hydrogenation process has a final boiling point of 300° C. or less and contains at least 2 carbon atoms per molecule and comprises at least one polyunsaturated compound. The term "polyunsaturated compounds" means compounds comprising at least one acetylene function and/or at least one diene function and/or at least one alkenylaromatic function.

More particularly, the feed is selected from the group constituted by a C2 cut from steam cracking, a C2-C3 cut from steam cracking, a C3 cut from steam cracking, a C4 cut from steam cracking and a C5 cut from steam cracking and a gasoline from steam cracking, which is also known as pyrolysis gasoline or C5+ cut.

The C2 cut from steam cracking, advantageously used in order to carry out the selective hydrogenation process in accordance with the invention, has the following composition, for example: in the range 40% to 95% by weight of ethylene, of the order of 0.1% to 5% by weight of acetylene, the remainder essentially being ethane and methane. In certain C2 cuts from steam cracking, between 0.1% and 1% by weight of C3 compounds may also be present. The C3 cut from steam cracking, advantageously used in order to carry out the selective hydrogenation process in accordance with the invention, has the following mean composition, for example: of the order of 90% by weight of propylene, of the order of 1% to 8% by weight of propadiene and of methylacetylene, the remainder essentially being propane. In certain C3 cuts, between 0.1% and 2% by weight of C2 compounds and C4 compounds may also be present.

A C2-C3 cut may also advantageously be used in order to carry out the selective hydrogenation process in accordance with the invention. It has the following composition, for example: of the order of 0.1% to 5% by weight of acetylene, of the order of 0.1% to 3% by weight of propadiene and of methylacetylene, of the order of 30% by weight of ethylene, of the order of 5% by weight of propylene, the remainder essentially being methane, ethane and propane. This feed may also contain between 0.1% and 2% by weight of C4 compounds.

The C4 cut from steam cracking advantageously used in order to carry out the selective hydrogenation process in accordance with the invention has the following mean composition by weight, for example: 1% by weight of butane, 46.5% by weight of butene, 51% by weight of butadiene, 1.3% by weight of vinylacetylene and 0.2% by weight of butyne. In certain C4 cuts, between 0.1% and 2% by weight of C3 compounds and C5 compounds may also be present.

The C5 cut from steam cracking advantageously used in order to carry out the selective hydrogenation process in accordance with the invention has the following composition, for example: 21% by weight of pentanes, 45% by weight of pentenes, and 34% by weight of pentadienes.

The gasoline from steam cracking or pyrolysis gasoline advantageously used in order to carry out the selective hydrogenation process in accordance with the invention corresponds to a hydrocarbon cut with a boiling point which is generally in the range 0° C. to 300° C., preferably in the range 10° C. to 250° C. In particular, the polyunsaturated hydrocarbons to be hydrogenated present in said gasoline from steam cracking are diolefinic compounds (butadiene, isoprene, cyclopentadiene, etc), styrene compounds (styrene, alpha-methylstyrene, etc) and indene compounds (indene, etc). The gasoline from steam cracking generally comprises the C5-C12 cut with traces of C3, C4, C13, C14, C15 (for example between 0.1% and 3% by weight for each of the cuts). As an example, a feed formed by pyrolysis gasoline generally has the following composition: 5% to 30% by weight of saturated compounds (paraffins and naphthenes), 40% to 80% by weight of aromatic compounds, 5% to 20% by weight of mono-olefins, 5% to 40% by weight of diolefins, 1% to 20% by weight of alkenylaromatic compounds, the total of the compounds forming 100%. It generally also contains 0 to 1000 ppm by weight of sulphur, preferably 0 to 500 ppm by weight of sulphur.

Preferably, the feed of polyunsaturated hydrocarbons treated using the selective hydrogenation process in accordance with the invention is a C2 cut from steam cracking, or a C2-C3 cut from steam cracking, or a gasoline from steam cracking.

The selective hydrogenation process in accordance with the invention is intended to eliminate said polyunsaturated hydrocarbons present in said feed to be hydrogenated without hydrogenating the monounsaturated hydrocarbons. As an example, when said feed is a C2 cut, the selective hydrogenation process is intended to selectively hydrogenate acetylene. When said feed is a C3 cut, the selective hydrogenation process is intended to selectively hydrogenate propadiene and methylacetylene. In the case of a C4 cut, butadiene, vinylacetylene (VAC) and butyne are to be eliminated, and in the case of a C5 cut, pentadienes are to be eliminated. When said feed is a gasoline from steam cracking, the selective hydrogenation process is intended to selectively hydrogenate said polyunsaturated hydrocarbons present in said feed to be treated in a manner such that the diolefinic compounds are partially hydrogenated into monoolefins and that the styrene and indene compounds are partially hydrogenated into the corresponding aromatic compounds, avoiding hydrogenation of the aromatic rings.

The technological implementation of the selective hydrogenation process is carried out by injection, for example, in an upflow or downflow mode, of the feed of polyunsaturated hydrocarbons and hydrogen into at least one fixed bed reactor. Said reactor may be of the isothermal or adiabatic type. An adiabatic reactor is preferred. The feed of polyunsaturated hydrocarbons may advantageously be diluted with one or more re-injection(s) of the effluent obtained from said reactor in which the selective hydrogenation reaction is carried out, at various points of the reactor located between the inlet and outlet for the reactor, in order to limit the temperature gradient in the reactor. The technological implementation of the selective hydrogenation process in accordance with the invention may also advantageously be carried out by installing at least said supported catalyst in a reactive distillation column or in the exchanger-reactors or in a slurry type reactor. The stream of hydrogen may be introduced at the same time as the feed to be hydrogenated and/or at one or more different points of the reactor.

The selective hydrogenation of the C2, C2-C3, C3, C4, C5 and C5+ cuts from steam cracking may be carried out in the gas phase or in the liquid phase, preferably in the liquid phase for the C3, C4, C5 and C5+ cuts and in the gas phase for the C2 and C2-C3 cuts. A liquid phase reaction can be used to reduce the energy costs and increase the contact time for the catalyst.

In general, the selective hydrogenation of a feed of hydrocarbons containing polyunsaturated compounds containing at least 2 carbon atoms per molecule and having a final boiling point of 300° C. or less is carried out at a temperature in the range 0° C. to 300° C., at a pressure in the range 0.1 to 10 MPa, at a molar ratio of hydrogen/(polyunsaturated compounds to be hydrogenated) in the range 0.1 to 10 and at an hourly space velocity HSV (defined as the ratio of the volume flow rate of feed over the volume of catalyst) in the range 0.1 to 200 $h^{-1}$ for a process carried out in the liquid phase, or at a molar ratio of hydrogen/(polyunsaturated compounds to be hydrogenated) in the range 0.5 to 1000 and at an hourly space velocity HSV in the range 100 to 40000 $h^{-1}$ for a process carried out in the gas phase.

In one embodiment in accordance with the invention, when a selective hydrogenation process is carried out in which the feed is a gasoline from steam cracking comprising polyunsaturated compounds, the molar ratio of (hydrogen)/(polyunsaturated compounds to be hydrogenated) is generally in the range 0.5 to 10, preferably in the range 0.7 to 5.0 and yet more preferably in the range 1.0 to 2.0, the temperature is in the range 0° C. to 200° C., preferably in the range 20° C. to 200° C. and more preferably in the range 30° C. to 180° C., the hourly space velocity (HSV) is generally in the range 0.5 to 100 $h^{-1}$, preferably in the range 1 to 50 $h^{-1}$ and the pressure is generally in the range 0.3 to 8.0 MPa, preferably in the range 1.0 to 7.0 MPa and more preferably in the range 1.5 to 4.0 MPa.

More preferably, a selective hydrogenation process is carried out in which the feed is a gasoline from steam cracking comprising polyunsaturated compounds, the molar ratio of hydrogen/(polyunsaturated compounds to be hydrogenated) is in the range 0.7 to 5.0, the temperature is in the range 20° C. to 200° C., the hourly space velocity (HSV) is generally in the range 1 to 50 $h^{-1}$ and the pressure is in the range 1.0 to 7.0 MPa.

Yet more preferably, a selective hydrogenation process is carried out in which the feed is a gasoline from steam cracking comprising polyunsaturated compounds, the molar ratio of hydrogen/(polyunsaturated compounds to be hydrogenated) is in the range 1.0 to 2.0, the temperature is in the range 30° C. to 180° C., the hourly space velocity (HSV) is generally in the range 1 to 50 $h^{-1}$ and the pressure is in the range 1.5 to 4.0 MPa.

The hydrogen flow rate is adjusted in order to have a sufficient quantity available to theoretically hydrogenate all of the polyunsaturated compounds and to maintain an excess of hydrogen at the reactor outlet.

In another embodiment in accordance with the invention, when a selective hydrogenation process is carried out in which the feed is a C2 cut from steam cracking and/or a C2-C3 cut from steam cracking comprising polyunsaturated compounds, the molar ratio of (hydrogen)/(polyunsaturated compounds to be hydrogenated) is generally in the range 0.5 to 1000, preferably in the range 0.7 to 800, the temperature is in the range 0° C. to 300° C., preferably in the range 15° C. to 280° C., the hourly space velocity (HSV) is generally in the range 100 to 40000 $h^{-1}$, preferably in the range 500 to 30000 $h^{-1}$ and the pressure is generally in the range 0.1 to 6.0 MPa, preferably in the range 0.2 to 5.0 MPa.

Description of the Catalyst

The catalyst employed to carry out the selective hydrogenation process in accordance with the invention comprises an active phase deposited on a support comprising alumina, said active phase being constituted by nickel. In accordance with the invention, the nickel element content in the catalyst is in the range 1% to 35% of the weight of the catalyst mass, preferably in the range 5% to 30% by weight, more preferably in the range 8% to 25% by weight, and yet more preferably in the range 13% to 23% by weight. The Ni content is measured by X-ray fluorescence.

The nickel is in the form of nanoparticles deposited on said support. The size of the nickel nanoparticles in the catalyst, measured in their oxide form, is 18 nm or less, preferably 15 nm or less, more preferably in the range 0.5 to 12 nm, and yet more preferably in the range 1.5 to 10.0 nm.

Said catalyst in accordance with the invention is generally present in all of the forms known to the person skilled in the art, for example in the form of beads, extrudates, tablets, pellets, hollow cylinders or irregular and non-spherical agglomerates the specific shape of which may result from a crushing step.

In a particular embodiment in accordance with the invention, the catalyst is constituted by extrudates with a general diameter in the range 0.5 to 10 mm, preferably in the range 0.8 to 3.2 mm and more preferably in the range 1.0 to 2.5 mm. It is advantageously present in the form of cylindrical, multi-lobed, trilobed or quadrilobed extrudates. Preferably, it is trilobal or quadrilobal in shape. The shape of the lobes could be adjusted using any of the methods known in the prior art.

In another particular embodiment in accordance with the invention, the catalyst is in the form of beads with a diameter in the range 1 to 8 mm, preferably in the range 2 to 7 mm.

The support on which said active phase is deposited comprises alumina ($Al_2O_3$).

In a first variation, the alumina present in said support is a transition alumina such as gamma, delta, theta, chi, rho, eta or kappa alumina, alone or as a mixture. More preferably, the alumina is a gamma, delta or theta transition alumina, alone or as a mixture.

In a second variation, the alumina present in said support is an alpha alumina.

The support may comprise another oxide which differs from the alumina, such as silica ($SiO_2$), titanium dioxide ($TiO_2$), cerine ($CeO_2$) or zirconia ($ZrO_2$). The support may be a silica-alumina. More preferably, said support is constituted solely by alumina.

The pore volume of the support is generally in the range 0.1 $cm^3/g$ to 1.5 $cm^3/g$, preferably in the range 0.5 $cm^3/g$ to 1.0 $cm^3/g$. The specific surface area of the support is generally 5 $m^2/g$ or higher, preferably 30 $m^2/g$ or higher, more preferably in the range 40 $m^2/g$ to 250 $m^2/g$, and yet more preferably in the range 50 $m^2/g$ to 200 $m^2/g$.

Description of the Catalyst Preparation Process

In general, the catalyst used in the context of the selective hydrogenation process is prepared by a process comprising at least the following steps:

i) a step for bringing said support into contact with at least one solution containing at least one precursor of nickel;

ii) a step for bringing said support into contact with at least one solution containing at least one organic compound comprising at least one amine function with the empirical formula $C_xN_yH_z$ in which $1 \leq x \leq 20$, $1 \leq y \leq x$, $2 \leq z \leq 2x+2$, or an amide function, or an amino acid, iii) a step for drying said impregnated support at a temperature of less than 250° C., in order to obtain a dried catalyst;

steps i) and ii) being carried out separately, in any order, or simultaneously.

Step i)—Contact of Nickel Precursor with the Support

The nickel may be deposited on said support in accordance with the implementation of said step i) using any method which is well known to the person skilled in the art. in particular, said step i) may be carried out by impregnation, dry or in excess, or in fact by deposition—precipitation, using methods which are well known to the person skilled in the art.

Said step i) is preferably carried out by impregnation of the support consisting, for example, by bringing said support into contact with at least one solution, which may be aqueous or organic (for example methanol or ethanol or phenol or acetone or toluene or dimethylsulphoxide (DMSO)), or in fact constituted by a mixture of water and at least one organic solvent containing at least one precursor of nickel which is at least partially in the dissolved state, or in fact by bringing said support into contact with at least one colloidal solution of at least one nickel precursor in the oxidized form (nanoparticles of nickel oxide, of oxy(hydroxide) or of hydroxide) or in the reduced form (metallic nanoparticles of reduced nickel). Preferably, the solution is aqueous. The pH of this solution could be modified by optionally adding an acid or a base. In accordance with another preferred variation, the aqueous solution may contain ammonia or ammonium ions, $NH_4^+$.

Preferably, said step i) is carried out by dry impregnation, which consists of bringing the catalyst support into contact with a solution containing at least one precursor of nickel, wherein the volume of the solution is in the range 0.25 to 1.5 times the pore volume of the support to be impregnated.

When the nickel precursor is introduced in aqueous solution, a nickel precursor which is in the form of the nitrate, carbonate, chloride, sulphate, hydroxide, hyroxycarbonate, formate, acetate or oxalate form, in the form of complexes formed with acetylacetonates, or in fact tetrammine or hexammine complexes or any other inorganic derivative which is soluble in aqueous solution is advantageously used and brought into contact with said support. Advantageously, nickel nitrate, nickel carbonate, nickel chloride, nickel hydroxide or nickel hydroxycarbonate is used as the precursor of nickel. More preferably, the nickel precursor is nickel nitrate, nickel carbonate or nickel hydroxide.

The quantities of the nickel precursor or precursors introduced into the solution are selected in a manner such that the total content of the nickel element is in the range 1% to 35% by weight of the catalyst mass, preferably in the range 5% to 30% by weight, more preferably in the range 8% to 25% by weight, and yet more preferably in the range 12% to 23% by weight.

In the embodiment in which step i) is carried out by impregnation, dry or in excess, preferably dry, impregnation of the nickel onto the support may advantageously be carried out via at least two cycles of impregnation using identical or different nickel precursors in each cycle. In this case, each impregnation is advantageously followed by drying and optionally by a heat treatment.

Step ii)—Contact of Organic Compound with the Support

Contact of said support with at least one solution containing at least one organic compound comprising at least one amine function with the empirical formula $C_xN_yH_z$ in which $1 \leq x \leq 20$, $1 \leq y \leq x$, $2 \leq z \leq 2x+2$, or an amide function, or an amino acid, in accordance with the implementation of said step ii), may be carried out using any method which is well known to the person skilled in the art. In particular, said step ii) may be carried out by impregnation, dry or in excess in accordance with methods which are well known to the person skilled in the art. Preferably, said step ii) is carried out by dry impregnation, which consists of bringing the support of the catalyst into contact with a volume of said solution in the range 0.25 to 1.5 times the pore volume of the support to be impregnated.

Said solution containing at least one organic compound, at least one amine function with the empirical formula $C_xN_yH_z$ in which $1 \leq x \leq 20$, $1 \leq y \leq x$, $2 \leq z \leq 2x+2$, or an amide function, or an amino acid, may be aqueous or organic (for example methanol or ethanol or phenol or acetone or toluene or dimethylsulphoxide (DMSO)), or in fact constituted by a mixture of water and at least one organic solvent. Said organic compound has already been dissolved at least in part in said solution to the desired concentration. Preferably, said solution is aqueous or contains ethanol. More preferably, said solution is aqueous. The pH of said solution may be modified by the optional addition of an acid or a base. In another possible embodiment, the solvent may be absent from the impregnation solution.

In the embodiment in which step ii) is carried out by impregnation, dry or in excess, preferably dry, impregnation of the support may be carried out by using one or more solutions wherein at least one of said solutions comprises at least one organic compound comprising at least one amine function with the formula $C_xN_yH_z$ in which $1 \leq x \leq 20$, $1 \leq y \leq x$, $2 \leq z \leq 2x+2$, or an amide function, or an amino acid.

In the embodiment in which step ii) is carried out by impregnation, dry or in excess, preferably dry, impregnation of the support may advantageously be carried out by means of at least two cycles of impregnation, by using organic compounds, or mixtures of organic compounds wherein at least one comprises at least one amine function with the empirical formula $C_xN_yH_z$ in which $1 \leq x \leq 20$, $1 \leq y \leq x$, $2 \leq z \leq 2x+2$, or an amide function, or an amino acid, which may be identical or different in each cycle. In this case, each impregnation is advantageously followed by drying and optionally by a heat treatment.

The molar ratio of said organic compound introduced during step ii) with respect to the nickel element introduced in step i) is in the range 0.01 to 1.5 mol/mol, preferably in the range 0.05 to 1.0 mol/mol, more preferably in the range 0.08 to 0.9 mol/mol.

Said organic compound contains in the range 1 to 20 carbon atoms, preferably in the range 1 to 14 carbon atoms, and yet more preferably in the range 2 to 8 carbon atoms.

In one embodiment in accordance with the invention, the organic compound comprises at least one amine function with the empirical formula $C_xN_yH_z$ in which x is in the range 1 to 20, $y=1-x$ and $z=2-(2x+2)$. Said organic compound may be selected from an aliphatic, cyclic, alicyclic, aromatic or heterocyclic, saturated or unsaturated amine optionally comprising alkyl or aryl substituents or alkyl substituents containing unsaturated bonds. The amine functions may be selected from primary, secondary and tertiary amines.

In accordance with a first variation, the organic compound comprises a single amine function and does not contain any other functional groups.

More particularly, said organic compound comprising a single amine function is selected from aliphatic compounds such as propylamine, ethylmethylamine, butylamine, dimethylisopropylamine, dipropylamine, diisopropylamine, octylamine, cyclic or alicyclic compounds such as cyclobutylamine, cyclohexylamine, aromatic compounds such as aniline, N,N-dimethylaniline, xylidines, saturated heterocyclic compounds such as piperidine, pyrrolidine, morpholine, or unsaturated heterocyclic compounds such as pyrrole, pyridine, indole, quinoline, said compounds possibly being substituted with one or more alkyl or aryl or alkyl group(s) containing unsaturated bonds.

In accordance with a second variation, the organic compound comprises two amine functions and does not contain any other functional groups.

More particularly, said organic compound comprising two amine functions is selected from aliphatic compounds such as ethylenediamine, 1,3-diaminopropane, 1,2-diaminopropane, diaminohexane, tetramethylenediamine, hexamethylenediamine, tetramethylethylenediamine, tetraethylethylenediamine, benzathine, xylylenediamines, diphenylethylenediamine, cyclic or alicyclic compounds such as 1,2-diaminocyclohexane, aromatic compounds such as phenylenediamines and their derivatives, 4,4'-diaminobiphenyl, 1,8-diaminonaphthalene, or heterocyclic compounds such as piperazine, imidazole, pyrimidine, or purine, said compounds possibly being substituted with one or more alkyl or aryl or alkyl group(s) containing unsaturated bonds. Preferably, said organic compound is selected from ethylenediamine, diaminohexane, tetramethylenediamine, hexamethylenediamine, tetramethylethylenediamine and tetraethylethylenediamine.

In accordance with a third variation, the organic compound comprises at least three amine functions and does not contain any other functional groups. More particularly, said compound is selected from diethylenetriamine and triethylenetetramine.

More particularly preferred organic compounds comprising at least one amine function with the empirical formula $C_xN_yH_z$ in which $1 \leq x \leq 20$, $1 \leq y \leq x$, $2 \leq z \leq 2x+2$ as mentioned above are ethylenediamine, diaminohexane, tetramethylenediamine, hexamethylenediamine, tetramethylethylenediamine, tetraethylethylenediamine, diethylenetriamine and triethylenetetramine.

In one embodiment in accordance with the invention, said organic compound comprises at least one amine function and at least one carboxylic acid function (amino acid). From among the amino acids, said organic compound may be selected from the following compounds: alanine, arginine, asparagine, pyroglutamic acid, citrulline, gabapentin, glutamine, histidine, isoleucine, isoglutamine, leucine, lysine, norvaline, ornithine, phenylalanine, proline, saccharopine, sarcosine, serine, threonine, tryptophan, tyrosine, valine, pyrrolysine, 2-aminoisobutyric acid, ethylene diamine tetraacetic acid (EDTA), in any one of their isomeric forms. When the compound is an amino acid, it is preferably selected from alanine, arginine, lysine, proline, serine, threonine and EDTA.

In another embodiment in accordance with the invention, said organic compound comprises at least one amide function selected from an acyclic amide function or a cyclic amide function, optionally comprising alkyl or aryl substituents or alkyl substituents containing unsaturated bonds. The amide functions may be selected from primary, secondary or tertiary amides.

In accordance with a first variation, the organic compound comprises at least one acyclic amide function.

Said organic compound may comprise a single amide function and not contain any other functional groups, such as formamide, N-methylformamide, N,N-dimethylformamide, N-ethylformamide, N,N-diethylformamide, N,N-dibutylformamide, N,N-diisopropylformamide, N,N-diphenylformamide, acetamide, N-methylacetamide, N,N-dimethylmethanamide, N,N-diethylacetamide, N,N-dimethylpropionamide, propanamide, N-ethyl-N-methylpropanamide, benzamide, or acetanilide, in any one of their isomeric forms. Preferably, said organic compound is selected from formamide, N-methylformamide, N,N-dimethylformamide, N-ethylformamide, N,N-diethylformamide, acetamide, N-methylacetamide, N,N-dimethylmethanamide, N,N-diethylacetamide, N,N-dimethylpropionamide and propanamide.

Said organic compound may comprise two amide functions and not contain any other functional groups; an example is tetraacetylethylenediamine.

In accordance with a second variation, the organic compound comprises at least one cyclic amide function such as 1-formylpyrrolidine, 1-formylpiperidine, or a lactam type amide function. Preferably, said organic compound is selected from β-lactam, γ-lactam, δ-lactam and ε-lactam and their derivatives, in any one of their isomeric forms. More preferably, said organic compound is selected from 2-pyrrolidone, N-methyl-2-pyrrolidone, γ-lactam and caprolactam, in any one of their isomeric forms.

In accordance with a third variation, said organic compound may comprise at least one amide function and at least one other function which differs from the amide function. Preferably, said organic compound comprises at least one amide function and at least one carboxylic acid function such as acetylleucine, N-acetylaspartic acid, aminohippuric acid, N-acetylglutamic acid, or 4-acetamidobenzoic acid, in any one of their isomeric forms.

Preferably, said organic compound comprises at least one amide function and at least one alcohol function such as glycolamide, lactamide, N,N-diethyl-2-hydroxyacetamide, 2-hydroxy-N-methylacetamide, 3-hydroxypropionamide, mandelamide, acetohydroxamic acid, butyrylhydroxamic acid, and bucetin, in any one of their isomeric forms. Preferably, said organic compound is selected from lactamide and glycolamide.

In accordance with a fourth variation, the organic compound comprises at least one amide function and at least one supplemental nitrogen heteroatom preferably selected from urea, N-methylurea, N,N'-dimethylurea, 1,1-dimethylurea and tetramethylurea, in any one of their isomeric forms.

More particularly preferred organic compounds comprising at least one of the above amide functions are formamide, N-methylformamide, N,N-dimethylformamide, N-ethylformamide, N,N-diethylformamide, acetamide, N-methylacetamide, N,N-dimethylmethanamide, N,N-diethylacetamide, N,N-dimethylpropionamide, propanamide, 2-pyrrolidone, N-methyl-2-pyrrolidone, γ-lactam, caprolactam, acetylleucine, N-acetylaspartic acid, aminohippuric acid, N-acetylglutamic acid, 4-acetamidobenzoic acid, lactamide and glycolamide, urea, N-methylurea, N,N'-dimethylurea, 1,1-dimethylurea and tetramethylurea, in any one of their isomeric forms.

All of the embodiments pertaining to the nature of said organic compound may be combined together as long as step ii) can be carried out by contact of said support with at least one solution containing at least one organic compound comprising at least one amine function with the empirical formula $C_xN_yH_z$ in which $1 \leq x \leq 20$, $1 \leq y \leq x$, $2 \leq z \leq 2x+2$, or an amide function, or an amino acid, and in particular at least one organic compound as cited above.

Implementation of Steps i) and ii)

The process for the preparation of the nickel catalyst encompasses several modes of implementation. They are in particular distinguished by the order of introduction of the organic compound and the nickel precursor, contact of the organic compound with the support possibly being carried out after contact of the nickel precursor with the support, before contact of the nickel precursor with the support or at the same time as bringing the nickel into contact with the support.

A first implementation consists of carrying out said step i) prior to said step ii).

A second implementation consists of carrying out said step ii) prior to said step i).

Each step i) and ii) for contact of the support with the nickel precursor (step i), and for contact of the support with at least one solution containing at least one organic compound (step ii), is carried out at least once and may advantageously be carried out several times, optionally in the presence of a nickel precursor and/or of an identical or different organic compound at each step i) and/or ii) respectively; any and all possible combinations of carrying out steps i) and ii) are included in the scope of the invention.

A third implementation consists of carrying out said step i) and said step ii) simultaneously (co-contacting). This implementation may advantageously comprise carrying out one or more steps i), optionally with a nickel precursor which is identical to or different from each step i). In particular, one or more steps i) advantageously precede and/or follow said co-contacting step. This implementation may also include several co-contacting steps: the steps i) and ii) are carried out simultaneously several times over, optionally in the presence of a precursor of nickel and/or of an identical or different organic compound at each co-contacting step.

Preferably, when the organic compound comprises at least one amine function with the formula $C_xN_yH_z$ in which $1 \leq x \leq 20$, $1 \leq y \leq x$, $2 \leq z \leq 2x+2$, step i) is carried out before step ii) or step ii) is carried out before step i). Preferably, step i) is carried out before step ii).

Preferably, when the organic compound is an amino acid, step i) is carried out before step ii) or step ii) is carried out before step i). Preferably, step i) is carried out before step ii).

Preferably, when said organic compound comprises at least one acyclic amide function, step i) is carried out before step ii) or step ii) is carried out before step i). Preferably, step i) is carried out before step ii).

Preferably, when said organic compound comprises at least one cyclic amide function or a lactam function, step ii) is carried out before step i) or steps i) and ii) are carried out simultaneously.

Preferably, when said organic compound comprises at least one amide function and at least one other function which differs from the amide function, and in particular a carboxylic acid function, or an alcohol function, or a supplemental nitrogen heteroatom, step i) is carried out before step ii), or steps i) and ii) are carried out simultaneously. Preferably, step i) is carried out before step ii).

Each contact step may preferably be followed by an intermediate drying step. The intermediate drying step is carried out at a temperature of less than 250° C., preferably in the range 15° C. to 240° C., more preferably in the range 30° C. to 220° C., yet more preferably in the range 50° C. to 200° C., and yet more preferably in the range 70° C. to 180° C. Advantageously, when an intermediate drying step is carried out, an intermediate calcining step may be carried out. The intermediate calcining step is carried out at a temperature in the range 250° C. to 1000° C., preferably in the range 250° C. to 750° C.

Advantageously, after each contact step, irrespective of whether it is a step for contact of the nickel precursor with the support, a step for contact of the organic compound with the support or a step for contact of the nickel precursor and the organic compound simultaneously with the support, the impregnated support can be allowed to mature, optionally before an intermediate drying step. Maturation means that the solution can become distributed homogeneously in the support. When a maturation step is carried out, said step is advantageously operated at atmospheric pressure or under reduced pressure, in an inert atmosphere or in an atmosphere containing oxygen or in an atmosphere containing water, and at a temperature in the range 10° C. to 50° C., and preferably at ambient temperature. In general, a maturation period of less than forty-eight hours and preferably in the range five minutes to five hours is sufficient. Longer periods are not excluded, but do not necessarily bring about an improvement.

Step iii)—Drying

In accordance with the drying step iii) when carrying out the preparation of the catalyst prepared in accordance with at least one implementation described above, the drying step is carried out at a temperature of less than 250° C., preferably in the range 15° C. to 240° C., more preferably in the range 30° C. to 220° C., yet more preferably in the range 50° C. to 200° C., and still more preferably in the range 70° C. to 180° C., for a typical period in the range 10 minutes to 24 hours. Longer periods are not excluded, but do not necessarily bring about an improvement.

The drying step may be carried out using any technique which is known to the person skilled in the art. It is advantageously carried out in an inert atmosphere or in an atmosphere containing oxygen or in a mixture of inert gas and oxygen. It is advantageously carried out at atmospheric pressure or under reduced pressure. Preferably, this step is carried out at atmospheric pressure and in the presence of air or nitrogen.

Step iv)—Calcining (Optional)

Optionally, at the end of the drying step iii), a step iv) for calcining is carried out at a temperature in the range 250° C. to 1000° C., preferably in the range 250° C. to 750° C., under an inert atmosphere or under an atmosphere containing oxygen. The duration of this heat treatment is generally in the range 15 minutes to 10 hours. Longer periods are not excluded, but do not necessarily bring about an improvement. After this treatment, the nickel of the active phase is thus in the oxide form and the catalyst now contains little or no more of the organic compound introduced during the synthesis thereof.

Step v)—Reduction Treatment (Optional)

Prior to using the catalyst in the catalytic reactor and carrying out a hydrogenation process, at least one step for reduction treatment v) is advantageously carried out after steps iii) or iv) in the presence of a reducing gas in a manner such as to obtain a catalyst comprising nickel which is at least partially in the metallic form.

This treatment can be used to activate said catalyst and form metallic particles, in particular nickel in the zero valent state. Said reduction treatment may be carried out in situ or ex situ, i.e. after or before charging the catalyst into the hydrogenation reactor. Said reduction treatment step v) may be carried out on the catalyst which may or may not have undergone the passivation step vi) described below.

The reducing gas is preferably hydrogen. The hydrogen may be used pure or as a mixture (for example a hydrogen/nitrogen or hydrogen/argon or hydrogen/methane mixture). In the case in which the hydrogen is used as a mixture, it may be used in any proportions.

Said reduction treatment is carried out at a temperature in the range 120° C. to 500° C., preferably in the range 150° C. to 450° C. When the catalyst does not undergo passivation, or undergoes a reduction treatment before passivation, the reduction treatment is carried out at a temperature in the range 180° C. to 500° C., preferably in the range 200° C. to 450° C., and more preferably in the range 350° C. to 450° C. When the catalyst has already undergone a passivation, the reduction treatment is generally carried out at a temperature in the range 120° C. to 350° C., preferably in the range 150° C. to 350° C.

The duration of the reduction treatment is generally in the range 2 to 40 hours, preferably in the range 3 to 30 hours. The temperature rise to the desired reduction temperature is generally slow, for example fixed at between 0.1 and 10° C./min, preferably in the range 0.3 to 7° C./min.

The flow rate of hydrogen, expressed in L/hour/gram of catalyst, is in the range 0.01 to 100 L/hour/gram of catalyst, preferably in the range 0.05 to 10 L/hour/gram of catalyst, more preferably in the range 0.1 to 5 L/hour/gram of catalyst.

Step vi)—Passivation (Optional)

Prior to being used in the catalytic reactor, the catalyst in accordance with the invention may optionally undergo a passivation step (step vi) using a sulphur-containing or oxygen-containing compound, or with $CO_2$, before or after the reduction treatment step v). This passivation step may be carried out ex situ or in situ. The passivation step is carried out by carrying out methods which are known to the person skilled in the art.

The passivation step using sulphur can be used to improve the selectivity of the catalysts and prevent runaway when commencing the use of fresh catalysts. Passivation generally consists of irreversibly poisoning the most virulent of the active sites of the nickel which exist on the fresh catalyst using sulphur, and thus of attenuating the activity of the catalyst in favour of its selectivity. The passivation step is carried out by carrying out methods which are known to the person skilled in the art, particular examples of which being one of the methods described in the patent documents EP 0 466 567, U.S. Pat. No. 5,153,163, FR 2 676 184, WO 2004/098774 and EP 0 707 890. The sulphur-containing compound is, for example, selected from the following compounds: thiophene, thiophane, alkylmonosulphides such as dimethylsulphide, diethylsulphide, dipropylsulphide and propylmethylsulphide, or in fact an organic disulphide with formula HO—$R_1$—S—S—$R_2$—OH such as dithiodiethanol with formula HO—$C_2H_4$—S—S—$C_2H_4$—OH (usually known as DEODS). The sulphur content is generally in the range 0.1% to 2% by weight of said element with respect to the mass of catalyst.

The step for passivation using an oxygen-containing compound or $CO_2$ is generally carried out after a prior high temperature reduction treatment, generally in the range 350° C. to 500° C., and can be used to preserve the metallic phase of the catalyst in the presence of air. A second reduction treatment at a lower temperature, generally in the range 120° C. to 350° C., is then generally carried out. The oxygen-containing compound is generally air or any other stream containing oxygen.

Before carrying out the selective hydrogenation process in accordance with the invention, the catalyst prepared in accordance with at least one of the embodiments described above, associated or otherwise with said step iv) and/or said step v) and/or said step vi), is either completely or at least partially freed from said organic compound. Introducing the organic compound during the preparation thereof allows the dispersion of the active phase to be increased, thereby leading to a more active and/or more selective catalyst.

The invention will now be illustrated in the following examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 16/63.092, filed Dec. 22, 2016, are incorporated by reference herein.

EXAMPLES

All of the catalysts prepared in Examples 2 to 10 were prepared with the same content of the element nickel. The support used to prepare each of these catalysts was a delta alumina with a pore volume of 0.67 mL/g and a BET specific surface area of 70 m$^2$/g.

Example 1

Preparation of Aqueous Solutions of Ni Precursors

A first aqueous solution of Ni precursors (solution S1) used to prepare catalysts A, B, D, I and J was prepared at 25° C. by dissolving 276 g of nickel nitrate Ni($NO_3$)$_2$.6$H_2O$ (supplied by Strem Chemicals®) in a volume of 100 mL of demineralized water. The solution S1 was obtained, for which the concentration of NiO was 19.0% by weight (with respect to the mass of the solution).

A second aqueous solution of Ni precursors (solution S2) used to prepare catalysts C, F, G and H was prepared at 25° C. by dissolving 151 g of nickel nitrate Ni($NO_3$)$_2$.6$H_2O$ (supplied by Strem Chemicals®) in a volume of 50 mL of demineralized water. The solution S2 was obtained, for which the concentration of NiO was 19.3% by weight (with respect to the mass of the solution).

Example 2 (Comparative)

Preparation of a Catalyst A by Impregnation of Nickel Nitrate with No Additive

The solution S1 prepared in Example 1 was dry impregnated onto 10 g of said alumina support. The solid obtained in this manner was then oven dried overnight at 120° C., then calcined in a flow of air of 1 L/h/g of catalyst at 450° C. for a period of 2 hours.

The calcined catalyst A prepared in this manner contained 13.8% by weight of the element nickel supported on alumina and it contained crystallites of nickel oxide with a mean diameter (determined by X ray diffraction from the width of the diffraction peak located at the angle) 2thêta=43° which was 19.1 nm.

Example 3 (Invention)

Preparation of a Catalyst B by Successive Impregnation of Nickel Nitrate then of (L)-lysine The catalyst B was prepared by impregnation of Ni nitrate onto said alumina support then by impregnation of (L)-lysine using a molar ratio {(L)-lysine/nickel} equal to 0.6. To this end, the solution S1 prepared in Example 1 was dry impregnated onto said alumina support. The solid B1 obtained in this manner was then oven dried overnight at 120° C. Next, an aqueous solution B' was prepared by dissolving 6.76 g of (L)-lysine (CAS 56-87-1, supplied by Sigma-Aldrich®, purity 98%) in 20 mL of demineralized water. This solution B' was then dry impregnated onto 10 g of solid B1 which had already been prepared. The solid obtained in this manner was then oven dried overnight at 120° C., then calcined in a flow of air of 1 L/h/g of catalyst at 450° C. for a period of 2 hours.

The calcined catalyst B prepared in this manner contained 13.8% by weight of the element nickel supported on alumina and it contained crystallites of nickel oxide with a mean diameter of 3.8 nm.

Example 4 (Invention)

Preparation of a Catalyst C by Successive Impregnation of Hexamethylenediamine then of Nickel Nitrate The catalyst C was prepared by impregnation of hexamethylenediamine onto said alumina support then by impregnation of Ni nitrate using a {hexamethylenediamine/nickel} molar ratio equal to 0.6.

To this end, an aqueous solution C' was prepared by dissolving 5.37 g of hexamethylenediamine (CAS 124-09-4, supplied by Sigma-Aldrich®, purity 98%) in 20 mL of demineralized water. This solution C' was then dry impregnated onto said alumina support. The solid C1 obtained in this manner was then oven dried overnight at 120° C. Next, the solution S2 prepared in Example 1 was dry impregnated onto 10 g of solid C1 which had already been prepared. The solid obtained in this manner was then oven dried overnight at 120° C., then calcined in a flow of air of 1 L/h/g of catalyst at 450° C. for a period of 2 hours.

The calcined catalyst C prepared in this manner contained 13.8% by weight of the element nickel supported on alumina and it contained crystallites of nickel oxide with a mean diameter of 7.1 nm.

Example 5 (Invention)

Preparation of a Catalyst D by Successive Impregnation of Nickel Nitrate then of Glycolamide The catalyst D was prepared by impregnation of Ni nitrate onto said alumina support then by impregnation of glycolamide using a {glycolamide/nickel} molar ratio equal to 0.6.

To this end, the solution S1 prepared in Example 1 was dry impregnated onto said alumina support. The solid D1 obtained in this manner was then oven dried overnight at 120° C. Next, an aqueous solution D' was prepared by dissolving 3.47 g of glycolamide (CAS 598-42-5, supplied by Sigma-Aldrich®, purity 98%) in 20 mL of demineralized water. This solution D' was then dry impregnated onto 10 g of solid D1 which had already been prepared. The solid obtained in this manner was then oven dried overnight at 120° C., then calcined in a flow of air of 1 L/h/g of catalyst at 450° C. for a period of 2 hours.

The calcined catalyst D prepared in this manner contained 13.8% by weight of the element nickel supported on alumina and it contained crystallites of nickel oxide with a mean diameter of 4.2 nm.

Example 6 (Invention)

Preparation of a Catalyst E by Co-impregnation of Nickel Nitrate and of Glycolamide The catalyst E was prepared by co-impregnation of nickel nitrate and of glycolamide onto said alumina support using a {glycolamide/nickel} molar ratio equal to 0.6.

To this end, an aqueous solution E' was prepared by dissolving 57.0 g of nickel nitrate $Ni(NO_3)_2.6H_2O$ (supplied by Strem Chemicals®) and 8.83 g of glycolamide (CAS 598-42-5, supplied by Sigma-Aldrich®, purity 98%) in 20 mL of demineralized water. This solution E' was then dry impregnated onto 10 g of said alumina support. The solid obtained in this manner was then oven dried overnight at 120° C., then calcined in a flow of air of 1 L/h/g of catalyst at 450° C. for a period of 2 hours.

The calcined catalyst E prepared in this manner contained 13.8% by weight of the element nickel supported on alumina and it contained crystallites of nickel oxide with a mean diameter of 3.5 nm.

Example 7 (Invention)

Preparation of a Catalyst F by Successive Impregnation of γ-lactam then of Nickel Nitrate The catalyst F was prepared by impregnation of γ-lactam onto said alumina support then by impregnation of Ni nitrate using a molar ratio {γ-lactam/nickel} equal to 0.6.

To this end, an aqueous solution F' was prepared by dissolving 3.94 g of γ-lactam (CAS 616-45-5, supplied by Sigma-Aldrich®) in 20 mL of demineralized water. This solution F' was then dry impregnated onto said alumina support. The solid F1 obtained in this manner was then oven dried overnight at 120° C. Next, the solution S2 prepared in Example 1 was dry impregnated onto 10 g of solid F1 which had already been prepared. The solid obtained in this manner was then oven dried overnight at 120° C., then calcined in a flow of air of 1 L/h/g of catalyst at 450° C. for a period of 2 hours.

The calcined catalyst F prepared in this manner contained 13.8% by weight of the element nickel supported on alumina and it contained crystallites of nickel oxide with a mean diameter of 5.2 nm.

Example 8 (Invention)

Preparation of a Catalyst G by Successive Impregnation of γ-lactam then of Nickel Nitrate, with a Ratio of Additive to Nickel of 0.08

The catalyst G was prepared by impregnation of γ-lactam onto said alumina support then by impregnation of Ni nitrate using a {γ-lactam/nickel} molar ratio equal to 0.08.

To this end, an aqueous solution G' was prepared by dissolving 0.53 g of γ-lactam (CAS 616-45-5, supplied by Sigma-Aldrich®) in 20 mL of demineralized water. This solution G' was then dry impregnated onto said alumina support. The solid G1 obtained in this manner was then oven dried overnight at 120° C. Next, the solution S2 prepared in Example 1 was dry impregnated onto 10 g of solid G1 which had already been prepared. The solid obtained in this manner was then oven dried overnight at 120° C., then calcined in a flow of air of 1 L/h/g of catalyst at 450° C. for a period of 2 hours.

The calcined catalyst G prepared in this manner contained 13.8% by weight of the element nickel supported on alumina and it contained crystallites of nickel oxide with a mean diameter of 7.6 nm.

Example 9 (Invention)

Preparation of a Catalyst H by Successive Impregnation of γ-lactam then of Nickel Nitrate, with a Ratio of Additive to Nickel of 0.9

The catalyst H was prepared by impregnation of γ-lactam onto said alumina support then by impregnation of Ni nitrate using a {γ-lactam/nickel} molar ratio equal to 0.9.

To this end, an aqueous solution H' was prepared by dissolving 5.90 g of γ-lactam (CAS 616-45-5, supplied by Sigma-Aldrich®) in 20 mL of demineralized water. This solution H' was then dry impregnated onto said alumina support. The solid H1 obtained in this manner was then oven dried overnight at 120° C. Next, the solution S2 prepared in Example 1 was dry impregnated onto 10 g of solid H1 which had already been prepared. The solid obtained in this manner was then oven dried overnight at 120° C., then calcined in a flow of air of 1 L/h/g of catalyst at 450° C. for a period of 2 hours.

The calcined catalyst H prepared in this manner contained 13.8% by weight of the element nickel supported on alumina and it contained crystallites of nickel oxide with a mean diameter of 4.8 nm.

Example 10 (Invention)

Preparation of a Catalyst I by Successive Impregnation of Nickel Nitrate then of N-methylacetamide The catalyst I was prepared by impregnation of Ni nitrate onto said alumina support then by impregnation of N-methylacetamide using a {N-methylacetamide/nickel} molar ratio equal to 0.6.

To this end, the solution S1 prepared in Example 1 was dry impregnated onto said alumina support. The solid I1 obtained in this manner was then oven dried overnight at 120° C. Next, an aqueous solution I' was prepared by dissolving 3.38 g of N-methylacetamide (CAS 79-16-3, supplied by Sigma-Aldrich®, purity 99%) in 20 mL of demineralized water. This solution I' was then dry impregnated onto 10 g of solid I1 which had already been prepared. The solid obtained in this manner was then oven dried overnight at 120° C., then calcined in a flow of air of 1 L/h/g of catalyst at 450° C. for a period of 2 hours.

The calcined catalyst I prepared in this manner contained 13.8% by weight of the element nickel supported on alumina and it contained crystallites of nickel oxide with a mean diameter of 5.7 nm.

Example 11 (Invention)

Preparation of a Catalyst J by Successive Impregnation of Nickel Nitrate then of N-methylacetamide, without Final Calcining The catalyst J was prepared by impregnation of Ni nitrate onto said alumina support then by impregnation of N-methylacetamide using a {N-methylacetamide/nickel} molar ratio equal to 0.6.

To this end, the solution S1 prepared in Example 1 was dry impregnated onto said alumina support. The solid J1 obtained in this manner was then oven dried overnight at 120° C. Next, an aqueous solution J' was prepared by dissolving 3.38 g of N-methylacetamide (CAS 79-16-3, supplied by Sigma-Aldrich®, purity 99%) in 20 mL of demineralized water. This solution J' was then dry impregnated onto 10 g of solid J1 which had already been prepared. The solid obtained in this manner was then oven dried overnight at 120° C., with no other heat treatment. The catalyst J was obtained.

In order to carry out the characterizations, a portion of this catalyst J was calcined in a flow of air of 1 L/h/g of catalyst at 450° C. for a period of 2 hours, in order to obtain the calcined catalyst J_calci. The calcined catalyst J_calci contained 13.8% by weight of the element nickel supported on alumina and it contained crystallites of nickel oxide with a mean diameter of 6.2 nm.

Example 11

Evaluation of the Catalytic Properties of the Catalysts a to J for the Selective Hydrogenation of a Mixture Containing Styrene and Isoprene The catalysts A to J described in the examples above were tested as regards the reaction for the selective hydrogenation of a mixture containing styrene and isoprene.

The composition of the feed to be selectively hydrogenated was as follows: 8% by weight of styrene (supplied by Sigma Aldrich®, purity 99%), 8% by weight of isoprene (supplied by Sigma Aldrich®, purity 99%), and 84% by weight of n-heptane (solvent) (supplied by VWR®, purity >99% chromanorm HPLC). This feed also contained very small amounts of sulphur-containing compounds: 10 ppm by weight of sulphur introduced in the form of pentanethiol (supplied by Fluka®, purity >97%) and 100 ppm by weight of sulphur introduced in the form of thiophene (supplied by Merck®, purity 99%). This composition correspondeds to the initial composition of the reaction mixture. This mixture of model molecules was representative of a pyrolysis gasoline.

The selective hydrogenation reaction was carried out in a 500 mL stainless steel autoclave provided with magnetic mechanical stirring and which could function under a maximum pressure of 100 bar (10 MPa) and temperatures in the range 5° C. to 200° C.

Prior to introducing it into the autoclave, a quantity of 3 mL of catalyst was reduced ex situ in a stream of hydrogen of 1 L/h/g of catalyst, at 400° C. for 16 hours (temperature ramp-up of 1° C./min), then it was transferred into the autoclave, with the exclusion of air. After adding 214 mL of n-heptane (supplied by VWR®, purity >99% chromanorm HPLC), the autoclave was closed, purged then pressurized to 35 bar (3.5 MPa) of hydrogen, and heated to the test temperature of 30° C. At time t=0, approximately 30 g of a mixture containing styrene, isoprene, n-heptane, pentanethiol and thiophene was introduced into the autoclave. The reaction mixture then had the composition described above and stirring was commenced at 1600 rpm. The pressure in the autoclave was kept constant at 35 bar (3.5 MPa) with the aid of a reservoir tank located upstream of the reactor.

The progress of the reaction was followed by taking samples from the reaction medium at regular time intervals: the styrene was hydrogenated into ethylbenzene without hydrogenation of the aromatic ring, and the isoprene was hydrogenated into methylbutenes. If the reaction was extended to longer than necessary, the methylbutenes were in turn hydrogenated into isopentane. The consumption of hydrogen was also monitored over time by the reduction in the pressure in a reservoir tank located upstream of the reactor. The catalytic activity was expressed in moles of $H_2$ consumed per minute and per gram of Ni.

The catalytic activities measured for catalysts A to J are recorded in Table 1 below. They are with respect to the catalytic activity measured for catalyst A ($A_{HYD1}$).

TABLE 1

Comparison of the selective hydrogenation performances of a mixture containing styrene and isoprene.

| Catalyst | Additive used | Mode of introduction of additive | Mean size of NiO crystallites (nm) | $A_{HYD1}$ (%) |
|---|---|---|---|---|
| A (not in accordance) | — | — | 19.1 | 100 |
| B (in accordance) | Lysine | Steps i) then ii) | 3.8 | 457 |
| C (in accordance) | Hexamethylenediamine | Steps ii) then i) | 7.1 | 268 |
| D (in accordance) | Glycolamide | Steps i) then ii) | 4.2 | 403 |
| E (in accordance) | Glycolamide | Steps i) and ii) simultaneously | 3.5 | 486 |
| F (in accordance) | γ-lactam | Steps ii) then i) | 5.2 | 352 |
| G (in accordance) | γ-lactam | Steps ii) then i) - Molar ratio additive/Ni = 0.08 | 7.6 | 250 |
| H (in accordance) | γ-lactam | Steps ii) then i) - Molar ratio additive/Ni = 0.9 | 4.8 | 386 |
| I (in accordance) | N-methylacetamide | Steps i) then ii) | 5.7 | 321 |
| J (in accordance) | N-methylacetamide | Steps i) then ii) - no calcining | 6.2 | 297 |

The results shown in Table 1 demonstrate that the catalysts B to J, prepared in the presence of an organic compound (containing at least one amine function with the empirical formula $C_xN_yH_z$ in which 1≤x≤20, 1≤y≤x, 2≤z≤2x+2, or at least one amide function, or at least one amino acid) are more active than the catalyst A prepared in the absence of this type of organic compound. This effect is linked to the reduction in the size of the particles of Ni.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process comprising selective hydrogenation of polyunsaturated compounds containing at least 2 carbon atoms per molecule, contained in a hydrocarbon feed that is a C2 cut from steam cracking, a C2-C3 cut from steam cracking, a C3 cut from steam cracking, a C4 cut from steam cracking, a C5 cut from steam cracking or gasolines from steam cracking, with a final boiling point of 300° C. or less, said process being carried out at a temperature in the range 0° C. to 300° C., at a pressure in the range 0.1 to 10 MPa, in liquid phase at a molar ratio of hydrogen/(polyunsaturated compounds to be hydrogenated) in the range 0.1 to 10 and at an hourly space velocity in the range 0.1 to 200 $h^{-1}$, or in gas phase at a molar ratio of hydrogen/(polyunsaturated compounds to be hydrogenated) in the range 0.5 to 1000 and at an hourly space velocity in the range 100 to 40000 $h^{-1}$, in the presence of a catalyst comprising a support formed from alumina and an active phase constituted by nickel, said catalyst being prepared by a process comprising at least:

i) bringing said support into contact with at least one solution containing at least one precursor of nickel;

ii) bringing said support into contact with at least one solution containing at least one organic compound having 1 to 20 carbon atoms and at least one amine function with the empirical formula $C_xN_yH_z$ in which 1≤x≤20, 1≤y≤x, 2≤z≤2x+2, or at least one amide function, or at least one amino acid, to produce an impregnated support, iii) drying said impregnated support at a temperature of less than 250° C. so as to obtain a dried catalyst comprising nickel in the form of nanoparticles measured, in oxide form, of 1.5 to 10.0 nm;

i) and ii) being carried out separately, in any order, or simultaneously.

2. The process as claimed in claim 1, further comprising at iv) at least one calcination of said dried catalyst obtained in iii) at a temperature in the range 250° C. to 1000° C.

3. The process as claimed in claim 1, wherein i) and ii) are carried out simultaneously.

4. The process as claimed in claim 1, wherein i) is carried out before ii).

5. The process as claimed in claim 1, wherein ii) is carried out before i).

6. The process as claimed in claim 1, wherein i) and/or ii) is (are) carried out by dry impregnation.

7. The process as claimed in claim 1, wherein the catalyst has a nickel content is in the range 1% to 35% by weight with respect to the total catalyst weight.

8. The process as claimed in claim 1, wherein the at least one organic compound is an amino acid.

9. The process as claimed in claim 1, wherein the at least one organic compound comprises at least one amide function that is an acyclic amide function or a cyclic amide function.

10. The process as claimed in claim 1, wherein the at least one organic compound comprises at least one amide function and at least one other function which differs from the at least one amide function, that is a carboxylic acid function or an alcohol function.

11. The process as claimed in claim 9, wherein the at least one organic compound furthermore comprises a supplemental nitrogen heteroatom and is urea, N-methylurea, N,N'-dimethylurea, 1,1-dimethylurea or tetramethylurea, in any one of their isomeric forms.

12. The process as claimed in claim 1, wherein the feed is a C2 cut from steam cracking or a C2-C3 cut from steam cracking, and in which process in a gas phase the molar ratio of (hydrogen)/(polyunsaturated compounds to be hydrogenated) is in the range 0.5 to 1000, the temperature is in the range 0° C. to 300° C., the hourly space velocity (HSV) is in the range 100 to 40000 $h^{-1}$, and the pressure is in the range 0.1 to 6.0 MPa.

13. The process as claimed in claim 1, wherein the feed is gasolines from steam cracking and in which process in a liquid phase the molar ratio of (hydrogen)/(polyunsaturated compounds to be hydrogenated) is in the range 0.5 to 10, the temperature is in the range 0° C. to 200° C., the hourly space velocity (HSV) is in the range 0.5 to 100 $h^{-1}$, and the pressure is in the range 0.3 to 8.0 MPa.

14. The process as claimed in claim 1, wherein the polyunsaturated compounds containing at least 2 carbon atoms per molecule are diolefins, acetylenes and/or alkenylaromatics.

15. The process as claimed in claim 1, carried out in gas phase.

16. The process as claimed in claim 1, carried out in liquid phase.

* * * * *